United States Patent [19]

Fennimore

[11] 4,150,744
[45] Apr. 24, 1979

[54] PACKAGING

[75] Inventor: Jack Fennimore, Welwyn Garden City, England

[73] Assignee: Smith & Nephew Pharmaceuticals Ltd., Hertfordshire, England

[21] Appl. No.: 854,349

[22] Filed: Nov. 23, 1977

Related U.S. Application Data

[63] Continuation of Ser. No. 662,031, Feb. 27, 1976, abandoned.

[51] Int. Cl.² .................. B65D 81/24; B65D 83/14
[52] U.S. Cl. .......................... 206/205; 206/363; 206/439; 206/484.1; 206/524.8
[58] Field of Search .............. 206/484, 439, 205, 210, 206/438, 363, 63.3, 530, 484.1, 524.8; 229/3.5; 222/107, 546, 551; 426/107, 126

[56] References Cited

U.S. PATENT DOCUMENTS

| 2,731,053 | 1/1956 | Lockhart | 222/546 |
|---|---|---|---|
| 2,849,739 | 9/1958 | Dresden | 222/546 |
| 3,032,182 | 5/1962 | Bechtold | 206/439 |
| 3,347,419 | 10/1967 | Brandt et al. | 222/107 |
| 3,616,190 | 10/1971 | Shaw | 229/3.5 MF |
| 3,958,721 | 5/1976 | Kushida et al. | 222/107 |
| 4,022,206 | 5/1977 | Hilleman et al. | 229/3.5 MF |
| 4,051,265 | 9/1977 | Kirshenbaum et al. | 426/107 |

Primary Examiner—William T. Dixson, Jr.
Attorney, Agent, or Firm—Dike, Bronstein, Roberts, Cushman & Pfund

[57] ABSTRACT

A light-sensitive and oxygen-sensitive liquid such as an adrenalin solution for ophthalmic use is sealed within a polymer vessel provided with a dropper spout, the closed vessel itself being sealed within a light-tight gas-impermeable envelope which is purged with a non-reactive gas or is under vacuum. The envelope is preferably a three-component laminate of nylon aluminum foil and polypropylene.

5 Claims, 1 Drawing Figure

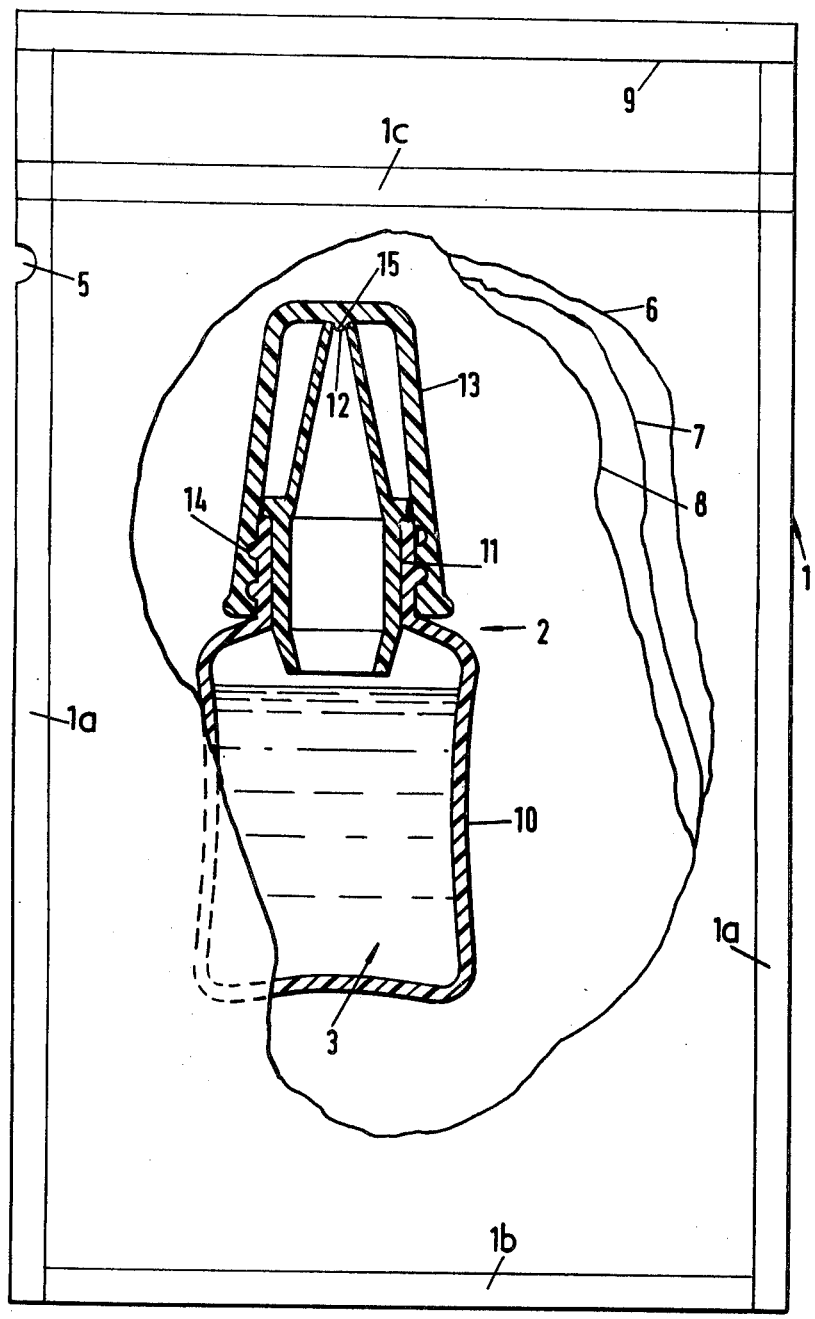

PACKAGING

This is a continuation, of application Ser. No. 662,031 filed Feb. 27, 1976 now abandoned.

This invention relates to the packaging of aqueous solutions for extended storage and subsequent dispensing, and has particular reference to the packaging of pharmacologically active solutions intended for topical application. In particular it is directed towards the storage and eventual use of solutions requiring protection from atmospheric oxidation such as stabilised catecholamine or N-acetylcysteine solutions for dropwise application to the eye.

For pharmaceutical use many solutions have to be made up under sterile conditions and presented either in small-capacity vessels for repeated topical application, or possibly in unit-dose containers for use and subsequent disposal.

Typically, such solutions are made up and filled into their containers under sterile conditions, stored for an extended period e.g. up to two years often with one or more periods of transport (e.g. manufacturer to hospital, hospital to patient) and dispensed over a shorter period such as two to four weeks multidose) or as a unit-dose application.

There is thus need to package and present such solutions in such a way as to limit or prevent deterioration due to light, breakage, loss or ingress of water vapour, bacterial contamination and oxidation by atmospheric oxygen whether in the "transport and storage" phase of their life or in the "use" phase. Light can be prevented from damaging the solution by packing in opaque containers, such as metal containers; however, there is then no way of determining how full the container is. Darkened transparent containers such as brown glass bottles have conventionally therefore been used. Proposals to use synthetic polymer containers have not found favour in this area since the polymer is usually transparent or translucent, and any attempt to render it opaque to ultraviolet light whether by pigmentation, fillers or ultraviolet-absorptive additives has either been technically infeasible or has led to the danger of leaching-out of pigment or additive into the solution on extended storage.

Breakage is to some extent a storage and transport problem but is particularly a "use" problem. Glass bottles, although readily pigmented (see above) are fragile in repeated use e.g. as eye-drops, especially when self-administered by a person of impaired vision.

Watervapour transmission can present itself as a disadvantage when aqueous medicament solutions are subject to extended storage. Glass bottles or, preferably, sealed ampoules overcome the problem but containers of synthetic polymer over, say, two years storage can lead to loss of more than 10% of contained water. Since many B.P. or U.S.P. medicinal formulations are made up to not more than 10% variation in solution strength of active ingredient, this loss is unacceptable.

Bacterial contamination, while not usually a problem over the storage period, can be a major problem on repeated use from a multidose container. For topical application it is common to use a dropper cap to a glass bottle of solution, so that air-carried bacteria have ingress to the bottle and access to the dropper, every time the solution is used. While this is conventionally dealt with by incorporation of an antibacterial agent, it is still good practice to minimise as far as possible the chances of such contamination.

Atmospheric oxygen can also deffuse into many types of containers over a lengthy storage period and lead to oxidative breakdown of any oxygen-sensitive ingredients. Where the containers are intended for subsequent multidose use this degradation can either lead to the solution being totally unsuitable for use even prior to opening the container or to a solution which deteriorates in only a few days after opening, leng before the complete contents of the opened bottle are used. This applies especially if any ingredient of an antioxidant nature is present in the solution; the container should resist the transmission of oxygen sufficiently to ensure that even after extended storage there is enough unused antioxidant to protect the solution when in use.

Glass bottles have higherto given the best results in this respect. Taking as example an aqueous solution containing 1% by weight adrenalin and 1% by weight of N-acetylcysteine, a sealed glass ampoule allowed no measurable oxidative degradation in six months, and a screw-top bottle (10 cc volume, 7.5 cc contents, filled under nitrogen, closed by an aluminium screw cap with a rubber liner faced with polyethylene terephthalate) gave, over several months measurement, readings equivalent to a projected 100% loss of N-acetylcysteine (NAC) in 20 months. At this stage, after the antioxidant characteristics of the NAC were used up, the adrenalin would react very quickly with any further oxygen diffusing through the cap, 7.5 micrograms being the quantity calculated for complete reaction to adrenochrome and other decomposition products with consequent loss of activity.

Such glass bottles are expensive and prone to breakage. However, attempts to use blowmoulded polymer bottles approximately 0.05 inches thick (1-1.5 mm) with the above solution led to a projected loss of 100% of the NAC in 5.7 weeks (polypropylene) and 7 weeks (polyethylene). Similar tests on a 5% NAC solution gave times for 100% projected loss of 27 weeks (polypropylene) and 62 weeks (nylon).

In addition to the above technical problems of lightstability, breakage, watervapour loss, bacterial contamination and oxidative degradation there is the practical and cost problems in prior art containers of providing (and protecting against breakage) a separate attachable squeeze-bulb dropper for incorporation into the neck of the glass vessel. It would be advantageous if the container itself could be squeezable and provided with an integral or at least permanently attached dropper, but as indicated above normal thicknesses of wall are too oxygen-permeable and thicker walls are too rigid to allow the container to be squeezed.

To overcome or minimise the above difficulties the present invention provides, as an article of commerce (A) a sealed light-tight gas-impermeable envelope any atmosphere inside which is oxygen-free (B) within the envelope at least one sealed liquid-retentive vessel having deformable walls of synthetic polymeric material and provided with a dropper spout with a closure removable to permit eventual dispensing of a contained liquid sealed therein, and (C) within the vessel a light-sensitive and oxygen-sensitive liquid.

The envelope in this combination resists entry of oxygen and light and loss of water vapour, thereby rendering the combination storable for long periods. The liquid-retentive vessel is however adequate to protect against loss and degradation for the much shorter period when the solution is in use.

The envelope is preferably a metal foil/polymer laminate, two layers of which can be heat-sealed, or RF-sealed to form a pouch, by the edges of its polymer surfaces. A typical laminate can have two layers but preferably possesses an additional outer polymer layer to facilitate abrasion resistance, or printing. The three-layer laminates typically consist, from the outside inwards, of (i) nylon, polyester polyethylene or polypropylene e.g. 10–70 g/m² thickness for abrasion resistance, etc. (ii) aluminium foil e.g. of 5–40 g/m² thickness and (iii) an inner heat-sealable polymer layer such as polyethylene, polypropylene, polyvinylidene chloride or nylon e.g. of 5–25 g/m² thickness. A nylon-foil-polypropylene laminate of e.g. 17 g/m² nylon, 32 g/m² aluminium and 45 g polypropylene, available under the Trade Name "STERILITE NFP" is particularly valuable.

Alternatively, but less preferably, the envelope can be a can or like container having an easily removed but impermeable lid or end.

In either case there is either a vacuum or an atmosphere of gas other than oxygen e.g. nitrogen or possibly carbon dioxide, within the envelope. Where a flexible foil envelope is used under vacuum nylon is especially preferred, and polyester less valuable as a protective outermost layer.

The flexible foil envelope, which can be e.g. from 6–15 cms wide by 10–20 cms long can if necessary include a tearstrip, tearing notch, line of weakness or like expedient to facilitate opening.

The liquid-retentive vessel can be one or more unit dose capsules which are cut (or torn) and squeezed into their desired site. Preferably however, it is a bottle, and made of polyolefin e.g. polypropylene or polyethylene. It may be blow-moulded with walls e.g. 0.5 to 2.0 mm thick. Its internal capacity can be between 5 and 30 ml. It can be formed with an integral dropper spout on one end or with a press-fit separate spout fitting into the neck of the bottle. In either case a tear-off end can be provided, but a screwcap over the end of the bottle is preferred, especially if some form of closure for the nozzle orifice is located inside the cap.

The liquid within the vessel preferably comprises an opthalmically acceptable solution such as a catecholamine such as adrenalin together with N-acetylcysteine, but may also be isoprenaline, phenylephrine, proxymetacaine, or physostigmine.

Preferably it comprises adrenalin (1% by weight) N-acetylcysteine (1% by weight) a buffering system to about pH 7 and a viscolizer and antibacterial agent. Optionally it contains quanethidine.

This invention will be further described with reference to the accompanying single figure of drawing which shows a partly torn away foil envelope containing a liquid-filled squeeze bottle shown in section.

The drawing shows a laminated foil envelope 1, enclosing a squeeze bottle of synthetic polymeric material 2 containing a liquid 3.

The laminated foil envelope 1 is heat sealed along each edge at 1a and along the bottom at 1b. An additional top seal 1c is provided and beneath this there is a tear notch 5 in one side of the envelope. By way of example the envelope may be formed as a laminate with (from the outside inwards) a nylon layer 6 (e.g. of weight 17 g/m²) an aluminium foil layer 7 (32 g/m²) and a polypropylene layer 8 (e.g. 45 g/m²). The various heat seals 1a, 1b and 1c can be ⅜" (9 to 10 mm) wide. The unsealed top portion 9 is a convenient location upon which the lot number or like indicia can be printed or stamped. The main body of the envelope can of course carry the makers name, trade mark or instructions for use.

The squeeze bottle 2 is formed in three parts. The container part 10 can be made by blow-moulding a polymer, for example polypropylene, and can be for instance onetwentieth of an inch (1.0–1.5 mm) in thickness. The nozzle 11 is pressfitted into neck of the bottle 10 and has a converging hollow stem terminating in orifice 12. The cap 13 is screw-threaded over the neck of the bottle 10 at 14 and possesses an internal protrusion 15 fitting into orifice 12 when screwed shut.

Liquid 3 is typically 7.5 ml of an aqueous adrenaline solution (1% by weight) containing N-acetylcysteine as an antioxidant (also 1% by weight) buffered by ammonium lactate/ammonium hydroxide to a pH near 7 and containing a hydroxyalkyl cellulose viscolizer and antibacterial agent such as a benzalkonium chloride.

The embodiment as shown in the above drawing can be manufactured in accordance with the following sequence of steps:-

1. The solution is made up and filled into the container 10 in aseptic conditions under a nitrogen atmosphere.

2. The nozzle 11 is pressed into place in the neck of container 10 (there is always a small amount of air within the nozzle cavity but this will be dealt with quickly by the antioxidant present).

3. The cap 13 is screwed into place.

4. The assembled bottle and contents are placed in the pouch which is formed by sealing the laminate at the sides 1a and bottom 1b. The sealing medium during pouch formation is the polypropylene laminated to the matt side of the foil. Heat seal temperature range is 230° C. to 260° C. with a dwell time of ¾ to 1 second and a pressure of 20 to 50 p.s.i. The sealing pressure is preferably followed by a consolidating pressure with unheated, but not cooled, jaws. Sealing jaws should be flat, teflon-covered, with a ¼" radius on the edge, and both sealing jaws should be heated.

5. This assembly is passed through a vacuum chamber to remove all air and optionally at this stage purged with nitrogen (suitable equipment is well known in the medical art under the trade name "Multivac").

6. The evacuated or optional nitrogen-purged assembly is heat sealed at 1c.

By way of comparison, a polypropylene bottle as described above, containing an aqueous solution of 1% adrenalin and 1% N-acetylcysteine, itself sealed into a laminate envelope as described above gave a 9% loss of NAC in the first month, a 4% loss in the next 12 months, and consequently a 100% projected NAC loss of many years. It appears that the initial loss is due to absorption of oxygen in the interstices of the nozzle and cap, and that subsequent loss is so slow that well over 50% NAC is still available after two years storage. This is ample to prevent adrenalin oxidation for a few weeks while the solution is in use.

I claim:

1. A packaged medicant comprising (1) an outer hermetically sealed envelope, (2) an inner dispenser bottle, and (3) an inert atmosphere within the envelope within which the dispenser bottle is immersed; said hermetically sealed envelope comprising a three-ply laminate wherein the outer ply is an abrasive-resistant polymer, an intermediate ply which is aluminum foil, and an inner ply which is a heat-sealable polymer, said three-ply laminate in combination excluding entry of oxygen and light and preventing escape of water vapor and the inert atmosphere; said inert atmosphere within the envelope being oxygen; free; and said dispensing bottle being a translucent polymer and containing a solution of light-sensitive, oxygensensitive medicant and an anti-oxident and comprising a receptacle for holding a predetermined quantity of the liquid medicant provided with a neck defining an opening to the interior of the receptacle, a discharge element comprising a cylindrical part press-fitted into the opening in the neck, a tapered nozzle through which the liquid medicant in the receptacle is adapted to be dispensed in predetermined doses, and an annular, externally-located collar in conjunction with the cylindrical part and the tapered nozzle for seating of the discharge element within the neck, said tapered nozzle terminating in an end opening of a diameter to dispense said predetermined dose and said receptacle having elastically flexible walls such as to enable squeezing the walls to displace a dose through the opening at the end of said tapered nozzle, a closure cap arranged to be releasably applied to the neck over the tapered nozzle and a sealing element interiorly of the cap arranged to become engaged with the opening at the end of the nozzle when the cap is applied to the neck to provide a leaktight barrier between the opening and the interior of the cap.

2. A package according to claim 1 containing a tear notch at one of its marginal edges to enable rupturing the envelope to afford access to the dispenser bottle.

3. A packaged medicant comprising a hermetically sealed envelope filled with an inert atmostphere and containing with the inert atmosphere a squeeze bottle dispenser containing a liquid solution of light-sensitive, oxygen-sensitive medicant and an anti-oxident; said envelope being comprised of a laminate of three plies, an outer ply of nylon which is abrasive-resistant, an intermediate ply of aluminum foil which is opaque and an inner ply of a heat-sealable polymer, said laminate excluding entry of oxygen and light into the envelope and preventing escape of the inert atmosphere and moisture from the envelope, said inert atmosphere within the envelope being oxygen-free and said squeeze bottle dispenser comprising a translucent body portion for holding a quantity of the solution and a nozzle part containing an end opening for dispensing the liquid medicant from the body part in predetermined doses, said body part having elastically-displaceable wall portions which may be squeezed to cause the liquid medicant to be dispensed in predetermined doses through the nozzle part and a cap applied to the body part over the nozzle part which, by engagement with the open end of the nozzle part, provides a barrier to the atmosphere within the cap around the nozzle.

4. A package according to claim 3 wherein the outer layer is 10–70 $g/m^2$, the intermediate layer is 5–50 $g/m^2$ and the inner layer is 5–25 $g/m^2$.

5. A package according to claim 3 wherein the liquid solution is adrenaline and N-acetyl-cysteine and wherein the oxidative loss is such that after two years storage at least 50% of the N-acetyl-cysteine remains.

* * * * *